United States Patent [19]

Kawamura

[11] 3,961,248

[45] June 1, 1976

[54] GAS DETECTOR USING GAS SENSING ELEMENTS EXHIBITING DIFFERENT RESPONSE CHARACTERISTICS

[75] Inventor: Masanori Kawamura, Chiba, Japan

[73] Assignee: Nohmi Bosai Kogyo Co. Ltd., Tokyo, Japan

[22] Filed: July 2, 1974

[21] Appl. No.: 485,140

[52] U.S. Cl. .................... 324/71 SN; 23/254 E
[51] Int. Cl.² .................................. G01N 31/06
[58] Field of Search ............... 324/71 SN, 65 R; 73/27 R; 23/232 E, 254 E, 255 E; 338/34

[56] References Cited
UNITED STATES PATENTS

| | | | |
|---|---|---|---|
| 2,583,930 | 1/1952 | Cotton | 324/65 R |
| 2,734,376 | 2/1956 | Cherry et al. | 23/255 E |
| 3,592,043 | 1/1971 | Munk | 23/254 E |
| 3,699,803 | 10/1972 | Sumi et al. | 324/71 SN |

OTHER PUBLICATIONS

Seiyama et al., "Study on a Detector for Gaseous Components using Semiconductive Thin Films," Analytical Chemistry vol. 38, No. 8, July, 1966, pp. 1069-1073.

*Primary Examiner*—John K. Corbin
*Assistant Examiner*—Wm. H. Punter
*Attorney, Agent, or Firm*—Wenderoth, Lind & Ponack

[57] ABSTRACT

A gas detector comprises a plurality of semiconductor gas detector elements each exhibiting a different sensitivity for at least one gaseous conponent. The elements are electrically combined in an electrical circuit to provide an output indicating the existence of a particular gas in an atmosphere.

5 Claims, 14 Drawing Figures

GAS DETECTOR USING GAS SENSING ELEMENTS EXHIBITING DIFFERENT RESPONSE CHARACTERISTICS

BACKGROUND OF THE INVENTION

1. Field of the Invention

This invention relates to gas detectors, and more particularly to gas detectors utilizing semiconductor gas sensing elements.

2. Description of the Prior Art

In order to detect dangerous gases such as a flammable gas and a poisonous gas contained in an atmosphere, various kinds of semiconductor gas detectors have been proposed and developed. FIG. 1 illustrates one example of typical conventional semiconductor gas detectors, which comprises a pair of input terminals 1 and 2 to be connected to a d.c. power source (not shown), a series combination of a resistor R and a semiconductor gas sensing element A connected across the input terminals 1 and 2, and a pair of output terminals 3 and 4 connected across the resistor R. Although not illustrated, the output terminals 3 and 4 are connected to a suitable means for indicating or recording the output voltage.

The semiconductor gas sensing element A is of one of the various kinds of well-known n-type reducing oxide semiconductor materials such as n-type tin oxide containing a small amount of a suitable catalyzer. The electrical resistance-to-gas characteristic of the sensing element, and, accordingly, the output voltage characteristic to gas of the gas detector in which the element is used, can be easily varied to a desirable characteristic only by changing the amount of the catalyzer added in the semiconductor material. The gas detector element generally has any suitable heating means $h$ for heating the sensing element to an elevated temperature for activation.

The gas detector illustrated in FIG. 1 exhibits the voltage-to-temperature characteristics across the output terminals 3 and 4 as shown by the several curves in FIG. 2. In the graph, the output voltage of the gas detector is plotted against various temperatures in centigrade. Curves P, H, M and I show the output voltages across the output terminals 3 and 4 when the gas detector is placed in an atmosphere of air containing a 1,000 ppm gaseous component of propane gas, hydrogen gas, methane gas and isobutane gas, respectively, with a voltage of 100V applied across the input terminals 1 and 2 and a resistance of 4 k$\Omega$ selected for the resistor R.

When, instead of the first gas sensing element A, another different second gas sensing element A' which contains a different amount of the catalyzer previously described is employed in the same gas detector circuit as illustrated in FIG. 1, the gas detector with the second gas sensing element A' exhibits output voltage-to-temperature characteristics for propane gas, hydrogen gas, methane gas and isobutane gas as shown in FIG. 3, which is quite different from that shown in FIG. 2. The characteristic curve P, H, M and I are those obtained under the same conditions as those in FIG. 2 except for the second gas sensing element A'.

From these characteristic curves shown in FIGS. 2 and 3, it is easily seen that with either one of the first and second sensing elements A and A', plural kinds of gaseous components are detected at the same time, thereby prohibiting the gas detector from selectively detecting a particular gaseous component to be detected. In some cases, it is impossible to detect dangerous gases such as a flammable gas and a poisonous gas through the use of the conventional gas detector employing a single semiconductor gas sensing element. Thus, the conventional gas detector is unsatisfactory or, in some cases, useless for those purposes. Also, the conventional gas detector is unable to identify the gaseous component detected and is unreliable and ineffective.

SUMMARY OF THE INVENTION

It is, therefore, a primary object of this invention to provide a new and improved gas detector capable of precisely discriminating gaseous components and while being highly reliable.

Another object of the invention is to provide a gas detector of simple structure employing conventional gas sensing elements.

These objects in view, the gas detector of the present invention comprises a pair of input terminals, a pair of output terminals, and an electrical circuit including a plurality of gas sensing elements connected between said input and output terminals, said gas sensing elements each having a different sensitivity for at least one of the gaseous components to be detected.

BRIEF DESCRIPTION OF THE DRAWING

The invention will become more readily apparent from the following exemplary description taken in conjunction with the accompanying drawings, in which.

It is to be noted that throughout the several Figures the same reference characteristics and numerals designate identical or corresponding components.

DESCRIPTION OF THE PREFERRED EMBODIMENTS

Figure 1:
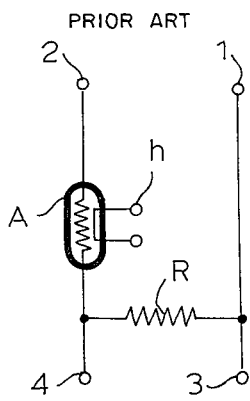
FIG. 1 is a circuit diagram of a conventional gas detector employing a single semiconductor gas sensing element.
Figure 3:
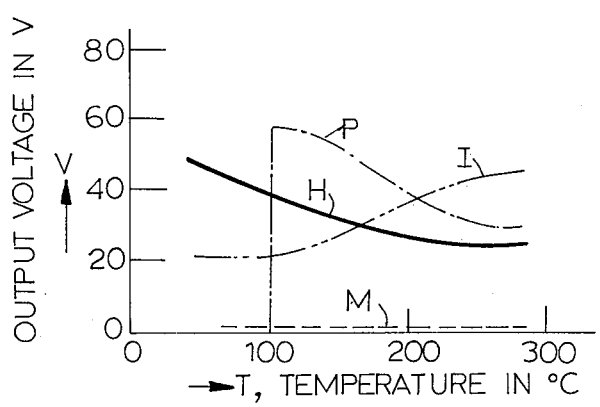
FIG. 3 shows the output voltage characteristics of another gas detector employing a different type of semiconductor gas sensing element.
Figure 4:
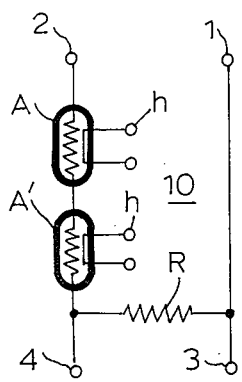
FIG. 4 is a circuit diagram of the gas detector of the present invention.

FIG. 4 illustrates a gas detector constructed in accordance with the invention, from which it is readily understood that the gas detector 10 of the invention is formed by merely inserting the second semiconductor gas sensing element A' of the type exhibiting the characteristics shown in FIG. 3 between the first sensing element A and a resistor R of 10kΩ in series therewith. In other respects, the circuit is the same as that shown in FIG. 1.

Figure 5:
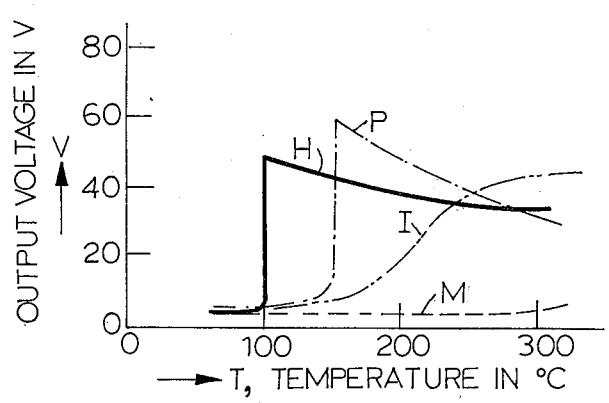
FIG. 5 is a graph showing output voltage-to-temperature characteristic curves for several gases of the gas detector shown in FIG. 4.

The gas detector 10 has output voltage-to-temperature characteristics for various gases across the output terminals 3 and 4 as shown in a graph of FIG. 5. From the graph, which is drawn in the same manner as in FIGS. 2 and 3, it is seen that the gas detector 10 comprising two different sensing elements A and A' has a sensitivity against hydrogen gas alone within a temperature range of from 100°C to 150°C. This is because both the first and second sensing elements A and A' provide an output voltage across the resistor R.

Figure 2:
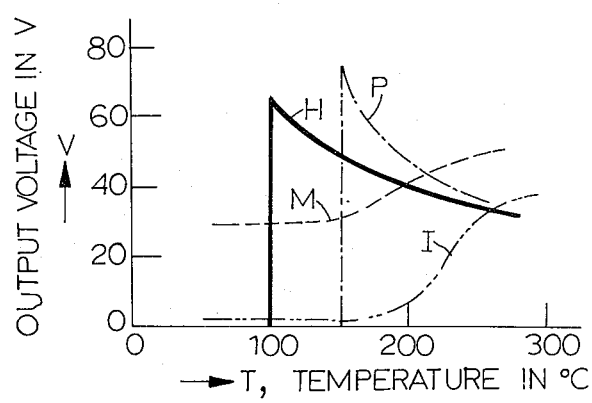
FIG. 2 shows the output voltage characteristics for several gases obtained by the gas detector shown in FIG. 1.

It will be easily understood that the gas detector 10 of the invention provides the output voltage-to-temprature characteristics for various gaseous components as shown in FIG. 5 taking into consideration that the serially connected first and second sensing elements A and A' which exhibit the characteristic curves as shown in FIGS. 2 and 3 respectively are inserted into the circuit. More specifically, when it is assumed that the total resistance value of the first and second detector elements A and A' of the gas detector 10 placed in an atmosphere of clear air is 100, then the resistance value of the resistor R will be about 10, and the total resistance value of the first and second sensing elements A and A' placed in an atmosphere of air containing any of the gases which can be detected by both the elements A and A' will be in the order of 1. Therefore, as seen from FIGS. 2 and 3 either one of the sensing elements A and A' can hardly detect the existence of hydrogen gas, methane gas, propane gas and isobutane gas and exhibits high resistance at a termperature blow 100°C, thus providing almost no output voltage across the resistor R as shown in FIG. 5. In a temperature range of from 100°C to 150°C, both the first and second sensing elements A and A' detect hydrogen gas alone and reduce their resistance values, providing an output voltage across the resistor R as seen from the curve H in FIG. 5. Above 150°C, both the sensing elements A and A' sense hydrogen gas, propane gas and isobutane gas, resulting in the respective output voltage across the resistor R. Since methane gas does not appreciably affect the sensitivity of the second detector element A' over the entire possible temperature range, it provides only a very small, negligible output voltage across the resistor R as shown by the curve M in FIG. 5.

Thus, with the gas detector 10 illustrated in FIG. 4 wherein two first and second sensing elements A and A' each having different characteristics are connected in series, together with the output resistor R, across the input terminals 1 and 2, even those gases that are detected by both the first and second sensing elements A and A' can provide output voltages across the output terminals 1 and 2. Alternatively, when too many of the kinds of gaseous components that are to be sensed by both the sensing sensing elements A and A' to distinguish any particular gas are contained in the atmosphere to be monitored, any desired number of gas sensing elements that have further different sensitivities or characteristics against gases may be additionally connected in series with the first and second sensing elements A and A', thereby improving the selectivity for gases of the gas detector.

Figure 6:
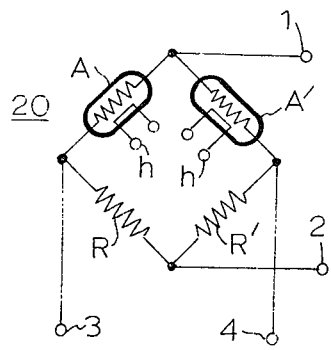
FIGS. 6 to 8 are circuit diagrams of modified gas detectors of the present invention.

FIG. 6 illustrates another embodiment of the gas detector 20 of the present invention, wherein a bridge circuit is composed of two resistors R and R' and two first and second gas sensing elements A and A' heated to about 130°C by any suitable heating means $h$. The elements A and A' are the same construction as those used in the circuit shown in FIG. 4 and are connected to form two adjacent sides of the bridge circuit. Through the use of the gas detector 20 of this construction, hydrogen gas which affects both the sensing elements A and A' cannot be sensed because the resistance variations of both the detector elements A and A' compensate for each other, while propane gas or methane gas can be sensed in the form of an output voltage appearing across the output terminals 3 and 4 because the equilibrium state of the bridge circuit is broken. The distinction between propane gas and methane gas can easily be made by determining the polarity of the output voltage.

Figure 7:
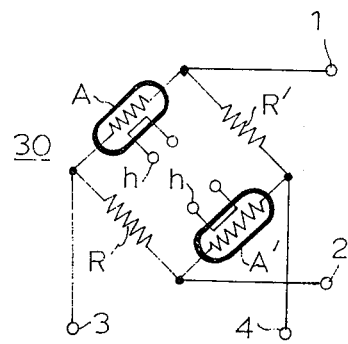

FIG. 7 illustrates another gas detector 30 constructed in accordance with the invention. The gas detector 30 is similar to the gas detector 20 shown in FIG. 6 except that the gas sensing elements A and A' are connected so as to form the two opposing sides of the bridge circuit and the resistors R and R' form the remaining sides accordingly. With this arrangement, by maintaining the gas sensing elements A and A' at a temperature of about 130°C, since the polarity of the output voltage at the pair of output terminals 3 and 4 of the detector 30 under the presence of a gaseous component, such as hydrogen, that can be sensed by both the elements A and A' is opposite to that in the clean air, the presence of the gaseous component can be very easily detected only by determining the polarity of the output voltage.

Figure 8:
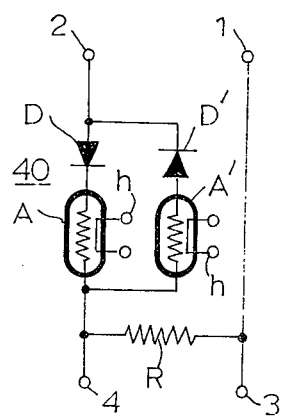

FIG. 8 illustrates a circuit diagram of a further modified gas detector 40 embodying the present invention. The gas detector 40 comprises two series connections composed of the first gas sensing element A and a diode D and the gas detector element A' and a diode D'. The diode D' is revesepoled with respect to the diode D, such that the series connections are connected in parallel with each other. An a.c. electric source of 100V (not shown) is connected at the input terminals 1 and 2. In other respects, the circuit is identical to that shown in FIG. 4.

Figure 9:
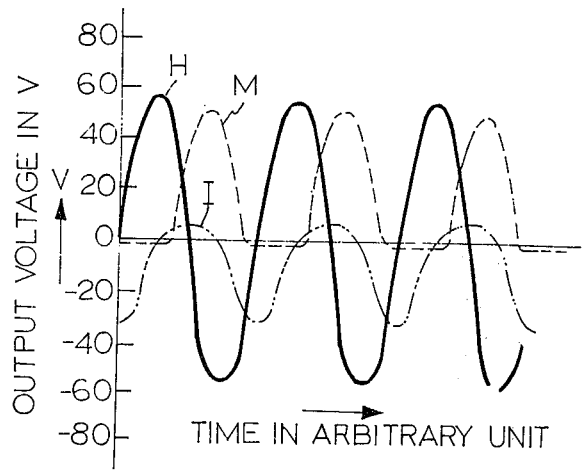
FIG. 9 is a graph showing output voltage-to-temperature characteristic curves for several gases obtained by the gas detector shown in FIG. 8.

FIG. 9 shows the output voltage waveform H, M and I appearing across the output terminals 3 and 4 of the gas detector 40 illustrated in FIG. 8 with an atmosphere containing 1,000 ppm of hydrogen gas, methane gas and isobutane gas, respectively. From the waveforms, it is seen that the curve H for hydrogen gas is substantially a full-wave commonly observed in a normal a.c. voltage, the curve M is substantially a positive half-wave, and that the curve I is substantially a negative half-wave. Thus, by determining the character or shape of the output voltage waveform across the terminals 3 and 4, the detected gaseous components in the atmosphere can easily be identified.

Figure 10:
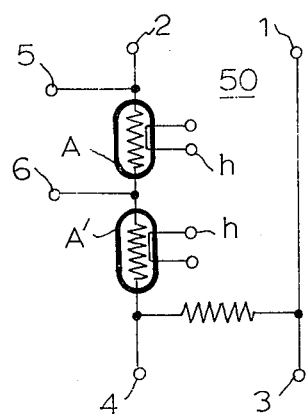
FIGS. 10 to 12 are circuit diagrams of additional modified gas detectors embodying the present invention.

Although only a single pair of output terminals 3 and 4 is utilized in the foregoing embodiments of the invention to provide necessary voltage values to detect the gases, it is to be noted that more than two pairs of output terminals may be utilized in order to detect and identify the gases. For example, as illustrated in FIG. 10, the gas detector 50 may be provided with a pair of output terminals 5 and 6 across the first detector element A. Other features of the gas detector 50 are identical to those of the gas detector 10 shown in FIG. 4. With this circuit arrangement, when the gas sensing elements A and A' are heated to about 130°C, and when the resistor R has a resistance of 10kΩ, the output voltages $V_R$ and $V_A$ given in the table below is established across the output terminals 3 and 4, and 5 and 6, respectively for pure air $A_i$ for 1,000 ppm gaseous componnents of hydrogen gas H, propane gas P, isobutane gas I and methane gas M.

|       | $A_i$ | H   | P   | I   | M  |
|-------|-------|-----|-----|-----|----|
| $V_A$ | 48V   | 16V | 86V | 76V | 4V |
| $V_R$ | 6V    | 48V | 8V  | 6V  | 4V |

As clearly seen from the above table, the output voltage $V_A$ for hydrogen gas H is smaller than that for the purified air $A_i$, while the output voltage $V_R$ for hydrogen gas H is higher than that of the purified air $A_i$. For propane gas P and isobutane gas I, the output voltage $V_A$ alone is substantial and only little output voltage $V_R$ is developed across the output terminals 3 and 4, and for methane gas M, almost no output voltage $V_A$ or $V_R$ is developed. Therefore, by using the above relationships in output voltages $V_R$ and $V_A$, individual detection of hydrogen, a compound of propane and isobutane, and methane can be achieved.

Figure 11:
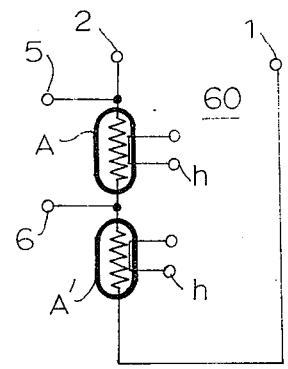

The gas detector 60 as illustrated in FIG. 11, wherein the resistor R and output terminals 3 and 4 are omitted from the circuit arrangement shown in FIG. 10, is capable of detecting gases by monitoring the output voltages developed across the sensing elements A and A'. More specifically, when the output voltage across the first element A is approximately equal to the source voltage the gas contained in the atmosphere is the one that cannot be sensed by the first sensing element A and that can be sensed by the second sensing element A'. When each of the first and second sensing elements A and A' develops an output voltage equally divided from the source voltage, it can be determined that the gas contained in the atmosphere is the one that cannot be detected by both the first and second sensing elements A and A' and that can be sensed by another detector element.

Figure 12:
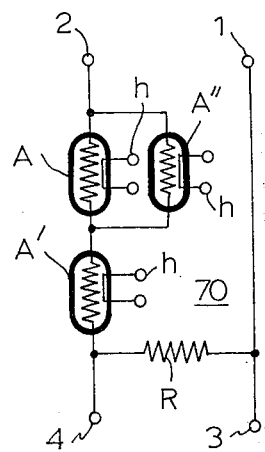

Further, the gas detector 70 as illustrated in FIG. 12, wherein one of the detector elements A or A' of the gas detector 10 shown in FIG. 4 is replaced by a plurality of parallel connected gas sensing elements exhibiting different sensitivities for different gaseous components, can be used to detect gaseous components in the atmosphere. When the voltage across the above-mentioned parallel connection is high enough, the gaseous component contained in the atmosphere is the one that cannot be sensed by any of the sensing elements connected in the parallel connection. When the output voltage across the parallel connection is substantially zero, the gas contained in the atmosphere is the one that can be sensed by either one of the sensing elements forming the parallel connection circuit.

Figure 14:
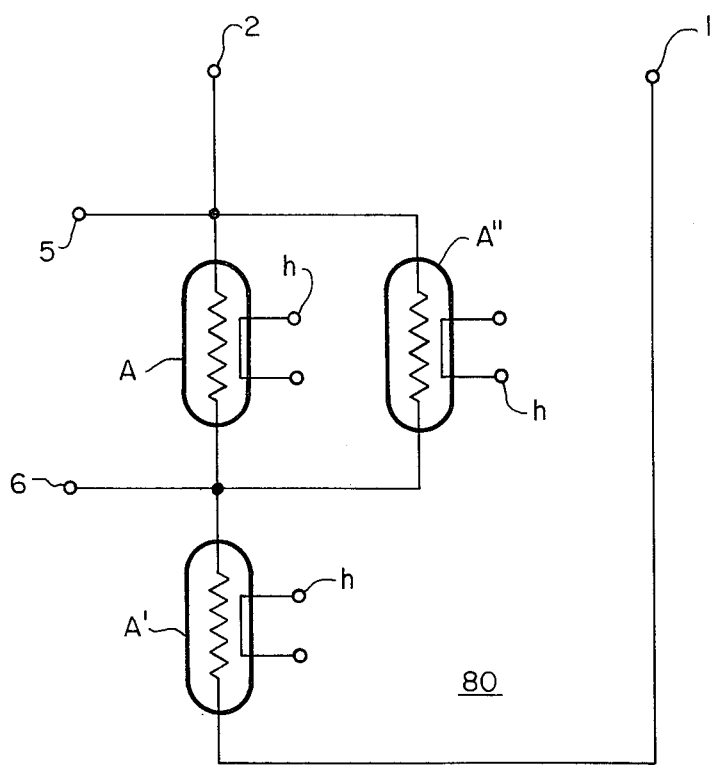
FIG. 14 is a circuit diagram of an additional modified gas detector of the present invention.

FIG. 14 illustrates another gas detector 80 of the present invention, wherein the gas sensing element A'' having gas response characteristics to a combination of a plurality of gaseous components different to the gas sensing element A shown in FIG. 11 is connected in parallel to the element A. When the voltage across the parallel connection of the gas sensing elements A and A'' is close to the source voltage, the gaseous component contained in the atmosphere is determined to be the one that is sensed by the gas sensing element A' and not by the gas sensing elements A and A''. When the source voltage is distributed across the elements A and A' in a predetermined proportion, the gas contained in the atmosphere is the one that cannot be sensed by either of the gas sensing element A, A' or A''. Further, in the event that the voltage across the parallel circuit including the elements A and A'' is of approximately zero value, the gaseous components contained in the atmosphere is the one that can be sensed either one of the elements A or A'' connected in the parallel circuit.

Figure 13:
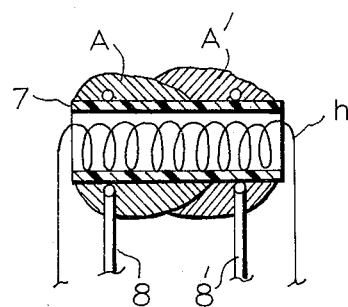
FIG. 13 is a sectional view showing the first and second gas sensing elements formed into a unitary structure.

Although the invention has been described in terms of the gas detectors of which sensing elements are of separate construction, it is to be noted that these sensing elements can be formed integrally, thereby enabling the gas detector to be compact, simple and easy to handle. FIG. 13 shows one such example, from which it is seen that the first and second sensing elements A and A' are formed integrally with each other. The integrally formed element of A and A' is supported by a hollow tubular porcelain member 7 through which a heater $h$ is inserted. Lead wires 8 and 8' are connected to the sensing elements A and A'.

When the parallel-connected sensing elements A and A' are desired to be formed into a unitary structure, one of the lead wires is embeded at the boundery between the sensing elements A and A' to provide connection to both the elements A and A' while the other of the lead wires is forked at its and connected to the respective elements A and A'.

What is claimed is:

1. A gas detector comprising:
   a pair of input terminals;
   a pair of output terminals; and
   an electrical circuit comprised of a plurality of gas sensing elements serially connected across said input terminals through a resistor connected across said output terminals, said gas sensing elements each having a different sensitivity for at least one of the gaseous components to be detected.

2. A gas detector as claimed in claim 1, wherein one of said gas sensing elements has a pair of output terminals connected thereacross.

3. A gas detector as claimed in claim 1, wherein one of said gas sensing elements has another gas sensing element connected in parallel thereto.

4. A gas detector comprising:
   a pair of input terminals;
   a pair of output terminals; and
   an electrical circuit comprised of a plurality of gas sensing elements connected in series with one another across said input terminals, said gas sensing elements each having a different sensitivity for at least one of the gaseous components to be detected, and one of said gas sensing elements having a pair of output terminals connected thereacross and another gas sensing element connected in parallel thereto.

5. A gas detector comprising a pair of input terminals, a pair of output terminals, and a parallel connection circuit connected across said input terminals through a resistor connected across said output terminals, said parallel connection circuit comprising two gas sensing elements each having a different sensitivity for at least one of gaseous components to be detected and connectdd in parallel with each other, and two diodes each connected in series with one of said gas sensing elements and poled in reverse direction each other.

* * * * *